United States Patent [19]

Akaike et al.

[11] Patent Number: 5,470,739
[45] Date of Patent: Nov. 28, 1995

[54] CELL CULTURE SUPPORT HAVING PATTERNED SUBSTANCE THAT INFLUENCES CELL ADHESION

[75] Inventors: Toshihiro Akaike; Seishiro Tobe, both of Kanagawa; Shigeyuki Miyamoto; Akio Ohashi, both of Tokyo, all of Japan

[73] Assignee: NEC Corporation, Tokyo, Japan

[21] Appl. No.: 994,685

[22] Filed: Dec. 22, 1992

[30] Foreign Application Priority Data

Dec. 26, 1991 [JP] Japan .................................. 3-357910

[51] Int. Cl.$^6$ .............................. C12M 3/00; C12N 5/00
[52] U.S. Cl. .................. 435/240.243; 435/240.1; 435/289.1; 435/283.1
[58] Field of Search ......................... 435/174, 176, 435/177, 178, 179, 180, 181, 182, 240.22, 240.243, 284, 240.1; 424/574

[56] References Cited

U.S. PATENT DOCUMENTS

| | | | |
|---|---|---|---|
| 4,645,669 | 2/1987 | Reid | 424/574 |
| 4,832,759 | 5/1989 | Curtis et al. | 435/287 |
| 4,921,803 | 5/1990 | Nohr | 435/288 |
| 4,956,289 | 9/1990 | Wrasidlo et al. | 435/240 |
| 4,963,489 | 10/1990 | Naughton et al. | 424/574 |
| 5,071,747 | 12/1991 | Hough et al. | 435/240.23 |
| 5,124,437 | 6/1992 | Akaike et al. | 530/322 |
| 5,324,591 | 6/1994 | Georger, Jr. et al. | 428/552 |

FOREIGN PATENT DOCUMENTS

| | | | |
|---|---|---|---|
| 2522014 | 8/1983 | France | 435/240.22 |
| 2150276 | 6/1990 | Japan | 435/240.22 |
| 2094832 | 3/1981 | United Kingdom | 435/240.22 |
| 8903228 | 4/1989 | WIPO | 424/574 |

OTHER PUBLICATIONS

*Neurosci.*, Kleinfeld et al., Nov. 1988(11):4098–4120.

Primary Examiner—Marian C. Knode
Assistant Examiner—Deborah K. Ware
Attorney, Agent, or Firm—Burns, Doane, Swecker & Mathis

[57] ABSTRACT

The invention discloses a cell culture support which provides for the adhesion and culturing of one or more adhesive cells using a photoresist in which to provide a particular patterned design on a surface of the support. The patterned design is provided by the photoresist which is partially removed by photolithography during the making of the support which in turn imparts a striped, checkerboard or dotted pattern on the surface of the support. Further, the cell culture support is produced by pretreating the support surface with a reagent to provide hydrophobicity to the support surface. Also a reagent can be added to pretreat the support surface in order to facilitate adhesion at the photoresist prior to applying the photoresist into the cell culture support. Collagen is applied in the form of a solution, containing in addition thereto albumin and a crosslinking agent, in order to form a film. Collagen specifically affects the cell adhesion rate or the morphology of the cells to be adhered to the support. The steps of applying a photoresist, partially removing it, providing hydrophobicity to the cell support surface, applying a solution to affect cell adhesiveness, film formation and dissolving the remaining photoresist are carried out repeatedly. In addition using a solution to promote film formation of a different film composition and thickness than the first is applied to produce the cell culture support. By varying the film composition a patterned design, such as checker board, is developed for purposes of providing a cell culture support for adherent cells.

21 Claims, 6 Drawing Sheets

CELL CULTURE SUPPORT HAVING PATTERNED SUBSTANCE THAT INFLUENCES CELL ADHESION

BACKGROUND OF THE INVENTION

The present invention relates to a cell culturing support and a process for fabricating the same.

At present, cell culture of various kinds of animals and plants is prevalent, and novel cell culture methods are being developed. The cell culture technique is utilized, for example, for elucidating the biochemical phenomena and nature of cells or for manufacturing useful substances. Further, attempts of investigating physiological activities or toxicity of the agents artificially synthesized using cultured cells.

Some of the cells, particularly most of the animal cells, have adhesion dependency in that they grow adhering onto something, and they cannot be kept alive for a long time in a floating state in vitro. Culturing of such cells having adhesion dependency requires a carrier on which the cells are to be adhered, and plastic Petri dishes coated uniformly with an adhesive protein such as collagen and fibronectin are generally employed for such purpose.

It is known that these adhesive proteins act Upon the culturing cells to influence the cell adhesion rate and cell adhesion form of the cells.

Further, various kinds of substances which specifically act on some sorts of cells have been found quite recently. For example, an artificial substrate material poly-N-vinyl-benzyl-D-lactonamide (PVLA) terminated with galactose is synthesized and utilized for hepatocyte culturing ("JINKO ZOKI (Artificial Organs)", vol. 19, No. 3 (1990) pp. 1156–1160). This artificial substrate material binds specifically hepatocytes and serves to maintain their spherical form.

Meanwhile, also reported is a technique in which cells to be cultured are adhered and arranged only onto a very small area of the support. Such technique enables application of the cultured cells to artificial internal organs, biosensors, bioreactors, etc. The most important technique in the patterning of culturing cells is the treatment of the cell culturing support, and some methods are currently tried.

For example, Japanese Unexamined Patent Publication No. 245181/1990 discloses application of an electric charge retaining medium having formed thereon an electrostatic charge pattern to cell culture. Meanwhile, Japanese Unexamined Patent Publication No. 7576/1991 discloses a technique of forming a hydrophilic or hydrophobic pattern on a support, in which a photosensitive hydrophilic polymer having no cell adhesiveness is patterned by photolithography in order to arrange cultured cells thereon as desired.

Meanwhile, Japanese Unexamined Patent Publication No. 7577/1991 discloses a technique of introducing a cell-adhesive functional group to the cell culture support, in which an ultraviolet ray or a radioactive ray is irradiated onto a cell culturing material having a cell-nonadhesive surface so as to introduce a cell-adhesive group thereto, or an ultraviolet ray or a radioactive ray is irradiated onto a cell culturing material to introduce a polymerization initiating species, followed by polymerization of a cell-adhesive or cell-nonadhesive monomer on said species.

The technique of patterning a functional organic film such as an enzyme film on the surface of a support is practically utilized in the field of biosensor manufacturing. For example, Japanese Patent Application No. 209165/1984 discloses patterning of an enzyme film by the lift-off method at the sensitive portion of a semiconductor ionsensor. The lift-off method consists of a step of applying a photoresist onto the surface of a sensor, a step of removing by photolithography the photoresist at a desired positions where an enzyme film is to be formed, a step of forming the enzyme film and a step of dissolving the photoresist.

The conventional cell culturing supports have a pattern formed by utilizing presence and absence of electrostatic charge or hydrophilicity/hydrophobicity difference. However, such support has only two types of surfaces, i.e. one to which cells adhere well and one to which cells do not substantially adhere, so that if cell culture is carried out using such support, only a simple pattern can be obtained depending on the feasibility of cell adhesion. In other words, no cell culturing support having a highly functional patterned surface, for example, a surface capable of showing various rates of cell adhesion and a surface capable of influencing the cell adhesion form, which is supposed to significantly influence the cell function, has yet been developed.

Meanwhile, the patterned surface formed by utilizing the presence and absence of electrostatic charge or hydrophilicity/hydrophobicity difference, can show a low selectivity depending on the kinds of cells. Accordingly, it is difficult to allow plural kinds of cells to adhere onto different surfaces respectively in the conventional supports.

With respect to fabrication of a cell culturing support, while photolithography using a photosensitive polymer is studied, there is disclosed no successful technique of directly patterning by photolithography a substance which influences the cell adhesion rate or cell adhesion form.

OBJECT AND SUMMARY OF THE INVENTION

Accordingly, it is an object of the invention to provide a cell culturing support having patterned thereon a substance which influences the cell adhesion rate or cell adhesion form and also a process for fabricating the same.

In order to attain the intended object, a first aspect of the invention is to provide a cell culturing support on which one or plural kinds of adhesive cells are adhered and cultured, characterized in that said support has on the surface thereof portions having adsorbed thereon a substance which specifically influences the cell adhesion rate or cell adhesion form.

The substance which specifically influences the cell adhesion rate or cell adhesion form can be exemplified by cell-adhesive proteins such as collagen, fibronectin, laminin and vitronectin.

The substance which specifically influences the cell adhesion rate or cell adhesion form also includes cell adhesive polymeric compounds such as poly-N-vinylbenzyl-D-lactonamide.

A second aspect of the invention is to provide a cell culturing support, on which one or plural kinds of adhesive cells are adhered and cultured, characterized in that said support has on the surface thereof a plurality of portions having adsorbed thereon a substance which specifically influences the cell adhesion rate or cell adhesion form, respectively, under the different conditions with respect to the kind of substance, composition or adsorption, A third aspect of the invention is to provide a cell culturing support, on which one or plural kinds of adhesive cells are adhered and cultured, characterized in that said support has on the surface thereof some portions having formed thereon a film which specifically influences the cell adhesion rate or cell adhesion form.

The film which specifically influences the cell adhesion rate or cell adhesion form can be formed by treating a cell-adhesive protein such as collagen, fibronectin, laminin and vitronectin with a crosslinking agent.

A fourth aspect of the invention is to provide a cell culturing support, on which one or plural kinds of adhesive cells are adhered and cultured, characterized in that said support has on the surface thereof plural kinds of portions having formed thereon a film which specifically influences the cell adhesion rate or cell adhesion form, respectively, under the different conditions with respect to the kind of substance, composition or film thickness.

A fifth aspect of the invention is to provide a cell culturing support, on which one or plural kinds of adhesive cells are adhered and cultured, characterized in that said support has on the surface thereof some portions having formed thereon a crosslinked albumin film containing a substance which specifically influences the cell adhesion rate or cell adhesion form.

The substance, constituting the film, which specifically influences the cell adhesion rate or cell adhesion form is a cell-adhesive protein including collagen, fibronectin, laminin and vitronectin.

The substance which specifically influences the cell adhesion rate or cell adhesion form also includes cell adhesive polymeric compounds such as poly-N-vinylbenzyl-D-lactonamide.

A sixth aspect of the invention is to provide a cell culturing support, on which one or plural kinds of adhesive cells are adhered and cultured, characterized in that said support has on the surface thereof a plurality of portions having formed thereon a crosslinked albumin film containing a substance which specifically influences the cell adhesion rate or cell adhesion form, respectively, under the different conditions with respect to the kind of substance, composition or film thickness.

A seventh aspect of the invention is to provide a process for fabricating a cell culturing support, on which one or plural kinds of adhesive cells are adhered and cultured, characterized in that said process consists of a step of applying a photoresist onto a support and then partly removing the photoresist by photolithography to partly expose the surface of the support, a step of adsorbing a substance which specifically influences the cell adhesion rate or cell adhesion form onto the support, and a step of dissolving the photoresist layer formed on the support.

An eighth aspect of the invention is to provide a process for fabricating a cell culturing support, on which one or plural kinds of adhesive cells are adhered and cultured, characterized in that said process consists of a step of applying a photoresist onto a support and then partly removing the photoresist by photolithography to partly expose the surface of the support, a step of adsorbing a substance which specifically influences the cell adhesion rate or cell adhesion form onto the support under the different conditions with respect to the kind of substance, composition or film thickness, and a step of dissolving the photoresist layer formed on the support, and that these steps are repeated.

A ninth aspect of the invention is to provide a process for fabricating a cell culturing support, on which one or plural kinds of adhesive cells are adhered and cultured, characterized in that said process consists of a step of applying a photoresist onto a support and then partly removing the photoresist by photolithography to partly expose the surface of the support, a step of forming a film which specifically influences the cell adhesion rate or cell adhesion form onto the support, and a step of dissolving the photoresist layer formed on the support.

A tenth aspect of the invention is to provide a process for fabricating a cell culturing support, on which one or plural kinds of adhesive cells are adhered and cultured, characterized in that said process consists of a step of applying a photoresist onto a support and then partly removing the photoresist by photolithography, a step of forming a film which specifically influences the cell adhesion rate or cell adhesion form onto the support, and a step of dissolving the photoresist layer formed on the support under the different conditions with respect to the kind of film, composition or film thickness, and that these steps are repeated.

An eleventh aspect of the invention is to provide a process for fabricating a cell culturing support, on which one or plural kinds of adhesive cells are adhered and cultured, characterized in that said process consists of a step of applying a photoresist onto a support and then partly removing the photoresist by photolithography, a step of applying a solution containing a substance which specifically influences the cell adhesion rate or cell adhesion form, albumin and a crosslinking agent onto the support to form a film, and a step of dissolving the photoresist layer formed on the support.

A twelfth aspect of the invention is to provide a process for fabricating a cell culturing support, on which one or plural kinds of adhesive cells are adhered and cultured, characterized in that said process consists of a step of applying a photoresist onto a support and then partly removing the photoresist by photolithography, a step of applying a solution containing a substance which specifically influences the cell adhesion rate or cell adhesion form, albumin and a crosslinking agent onto the support to form a film, and a step of dissolving the photoresist layer formed on the support under the different conditions with respect to the kind of film, composition and film thickness, and that these steps are repeated.

The cell culturing support according to the present invention has adsorbed thereon a substance which influences the cell adhesion rate or cell adhesion form, or has formed thereon a crosslinked albumin film containing such substance or a film which influences the cell adhesion rate or cell adhesion form, and a pattern is formed thereon by various kinds of highly functional surfaces, such as surfaces having different cell adhesions or rates and surfaces which influence the cell adhesion rates or cell adhesion form. Cells can be adhered onto the desired positions of the support at a desired cell adhesion rate or in a desired cell adhesion form and cultured, using the support of the present invention.

The support of the invention has a pattern specific to the kind of cells, making it possible to allow plural kinds of cells to adhere at different positions respectively onto the surface by culturing plural kinds of cells thereon.

Meanwhile, according to the process for fabricating the cell culturing support of the invention, a substance which influences the cell adhesion rate or cell adhesion form, a crosslinked albumin film containing such substance or a film which influences the cell adhesion rate or cell adhesion form can directly be patterned onto a support at desired positions by means of photolithography. The process for fabricating the cell culturing support of the invention, which resorts to the lift-off method using a photoresist, can also be applied to patterning of various kinds of substances as well as the photosensitive substances as used herein.

BRIEF DESCRIPTION OF THE DRAWINGS

The features of this invention that are believed to be novel are set forth with particularity in the appended claims. The invention, together with the objects and advantages thereof, may best be understood by reference to the following description of the preferred embodiments taken in conjunction with the accompanying drawings in which:

DETAILED DESCRIPTION OF PREFERRED EMBODIMENTS

Figure 1:
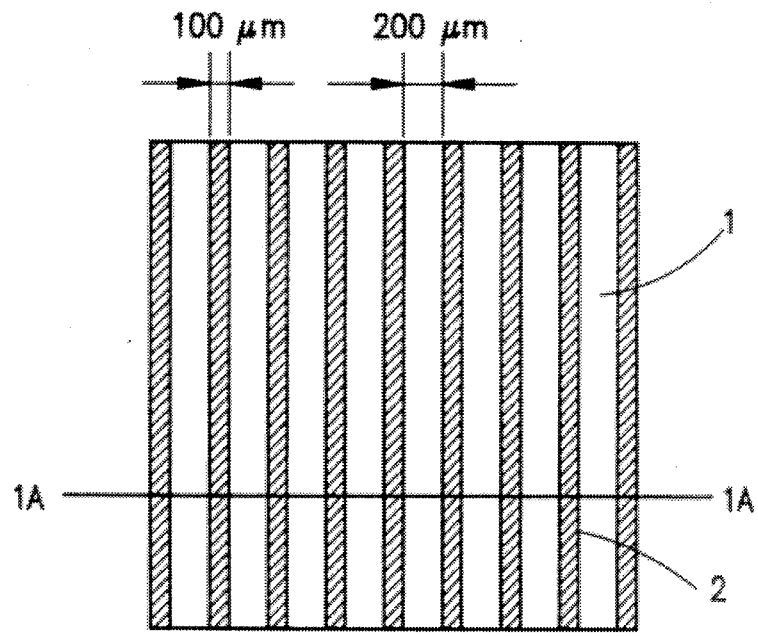
FIG. 1(a) shows a plan view of the cell culturing support according to one embodiment of the invention and a cross section taken along the line A—A of the plan view.
FIG. 1(b) is a microscopic view of the surface of the support shown in FIG. 1 on which hepatocytes of an adult rat were cultured.
Figure 1A:
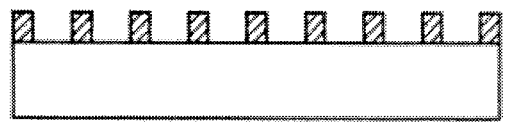

Preferred embodiments of the invention will now be described below referring to the attached drawings. FIG. 1(a) shows the cell culturing support according to a first embodiment of the invention.

The support body is of a quartz plate 1 having a thickness of 0.5 mm. The surface of the support has adsorbed thereon collagen 2 in a stripe pattern with a stripe (collagen) width of 100 µm and an interval (quartz) width of 200 µm. Collagen is a cell adhesive protein which participates in cell adhesion. Incidentally, hepatic cells assume a stretched form on collagen.

Figure 1B:
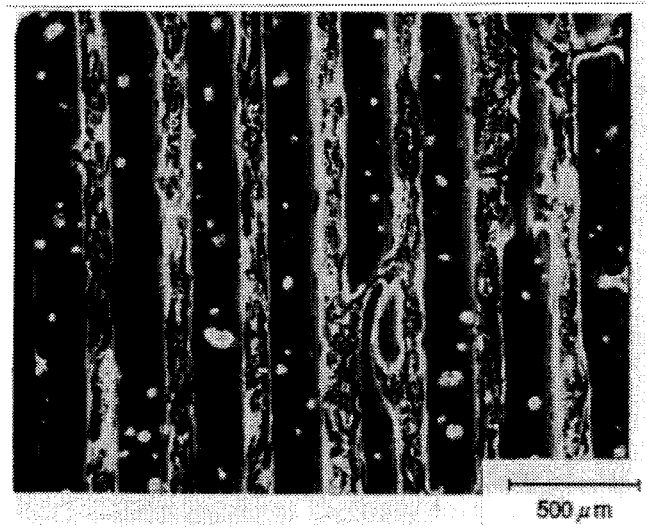

FIG. 1(b) shows the surface appearance of the support after hepatocytes of an adult rat were cultured thereon. The culturing was carried out using Williams' E medium at 37° C. in a 5% carbon dioxide gas atmosphere for 48 hours. Substantially all of the hepatic cells adhered onto the surface of collagen 2 rather than on the quartz surface. Besides, the cells adhered onto the collagen assume a spread form, and thus it can be seen that the collagen pattern adsorbed onto the quartz support is formed in such a state that it can maintain its original properties.

Figure 2:
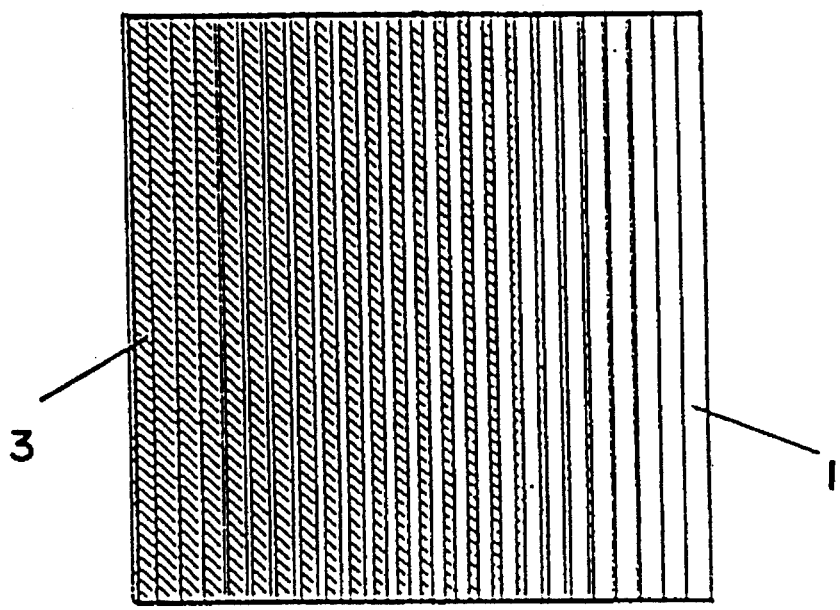
FIG. 2 shows the cell culturing support according to another embodiment of the invention.

FIG. 2 shows a variation of the cell culturing support according to the first embodiment of the invention. The surface of the quartz plate 1 has adsorbed thereon PVLA 3 in a stripe pattern in which the stripe (PVLA) width is incrementally increased by 4 µm while the interval (quartz) width is incrementally decreased by 4 µm, and the total of one stripe and one interval, which are adjacent to each other, is designed to be 100 µm. PVLA is an artificial substrate material to which hepatocytes specifically adhere. The hepatocytes assume a form of aggregate on PVLA.

Glass or quartz, metals such as silicon, and plastics such as polystyrene can be used as the cell culturing support body. Transparent glass, quartz and polystyrene can particularly suitably be used for monitoring the culturing cells using a transmission biological microscope.

The substance to be adsorbed onto the cell culturing support may not be limited to collagen 2 or PVLA 3, and any other substances which can specifically influence the culturing cells adhered thereon and which can be adsorbed onto the support can be used.

Such substance includes, for example, cell-adhesive proteins such as fibronectin, laminin and vitronectin; artificial substrate materials which participate in cell adhesion such as polystyrene derivatives having an oligosaccharide chain in the side chain, e.g. glucose and maltose; and polysaccharides such as galactan, mannan and mucopolysaccharide. Besides, proteins such as bovine serum albumin or polyamino acids such as polylysine and polyglutamic acid can also be used as such substance.

Figure 3:
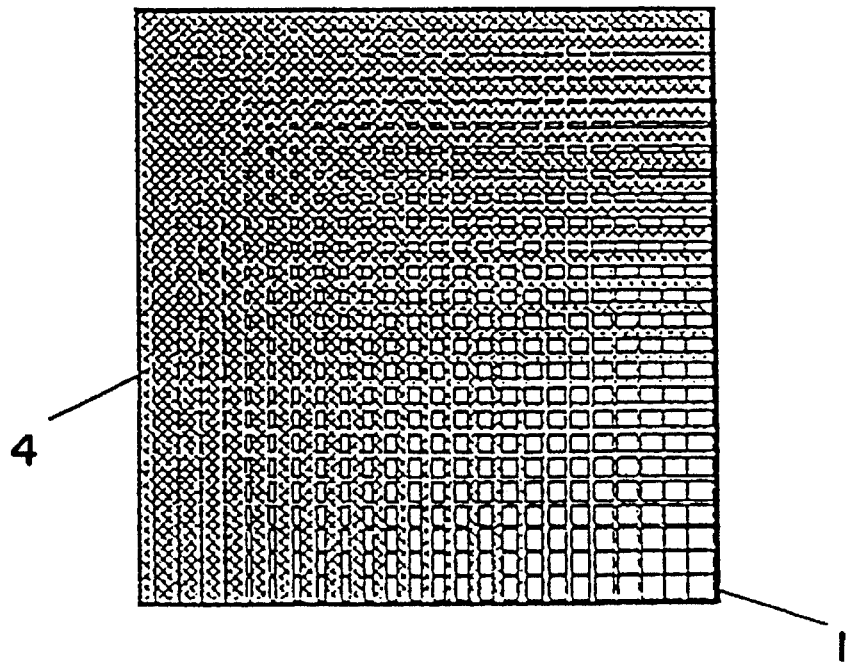
FIG. 3 shows the cell culturing support according to a further embodiment of the invention.

FIG. 3 shows the cell culturing support according to another embodiment of the invention. The surface of the quartz plate 1 has formed thereon a collagen film 4 crosslinked with glutaraldehyde in a cross stripe pattern in which the stripe (collagen) width is incrementally increased by 4 µm, both widthwise and lengthwise, while the interval (quartz) width is likewise incrementally decreased by 4 µm, and the total of one stripe and one interval, which are adjacent to each other, is designed to be 100 µm.

The film to be formed onto the cell culturing support may include, in addition to the glutaraldehyde-crosslinked collagen film 4, those of cell-adhesive proteins such as fibronectin, laminin and vitronectin.

Figure 4:
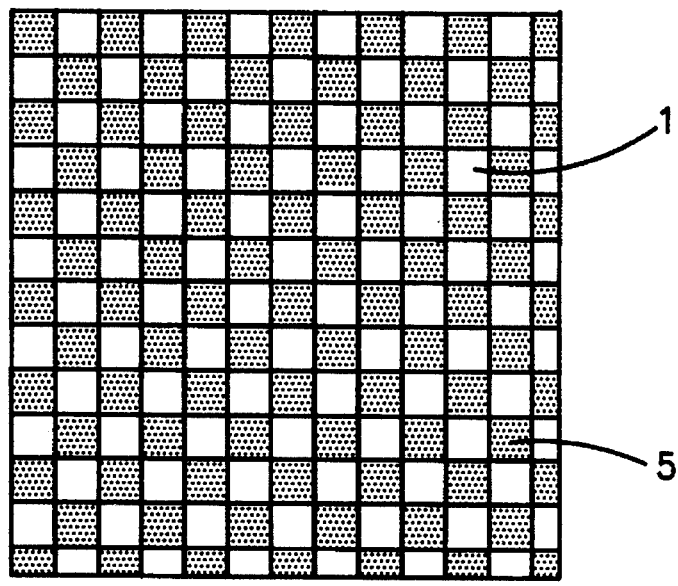
FIG. 4 shows the cell culturing support according to still another embodiment of the invention.

FIG. 4 shows the cell culturing support according to another embodiment of the invention. The surface of the quartz plate 1 has formed thereon a crosslinked albumin film 5 containing collagen in a checkered pattern (unit square: 200 µm×200 µm).

The crosslinked albumin film 5 to be formed on the cell culturing support sufficiently contains a substance which specifically influences the culturing cells. The substance which specifically influences the culturing cells includes those which can be adsorbed onto the cell culturing support, as described referring to the first embodiment.

Figure 5:
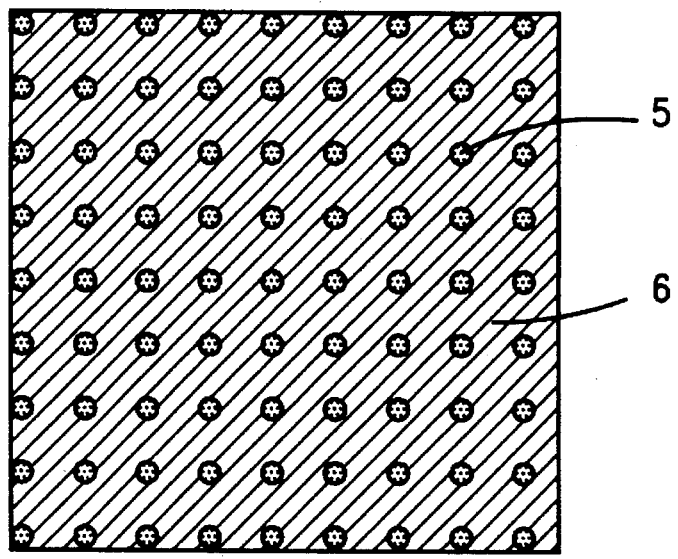
FIG. 5 shows the cell culturing support according to another embodiment of the invention.

FIG. 5 shows the cell culturing support according to another embodiment of the invention. The surface of the quartz plate 1 has formed thereon a crosslinked albumin film 5 containing collagen in a circular insular pattern or polka dotted pattern (dot diameter: 100 µm) at 200 µm intervals and the rest of the portion is coated with a crosslinked albumin film containing PVLA.

As described above, it will be apparent that the cell culturing support having formed on the surface thereof a combination of portions coated with crosslinked albumin films 5 and 6 containing different substances is useful and that one having adsorbed thereon a combination of different substances and one having formed thereon a combination of different films are also useful. Moreover, it is also possible to use a variety of combinations of a surface having adsorbed thereon a substance which specifically influences the cells, a crosslinked albumin film containing such substance and a film which specifically influences the cells.

Figure 6A:
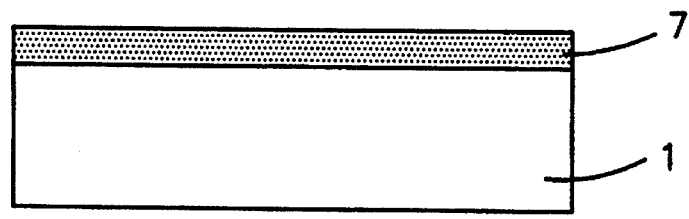
FIGS. 6(a) to (d) show a process for fabricating the cell culturing support according to one embodiment of the invention.

FIGS. 6(a) to (d) are a flow diagram illustrating a process for fabricating the cell culturing support according to one embodiment of the invention. The process will be described below step by step. A clarified quartz plate 1 is used as a support, and a photoresist 7 is first applied by spin coating and dried, as shown in FIG. 6(a).

Figure 6B:
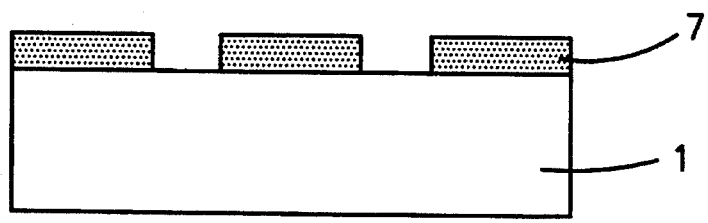
Figure 6C:
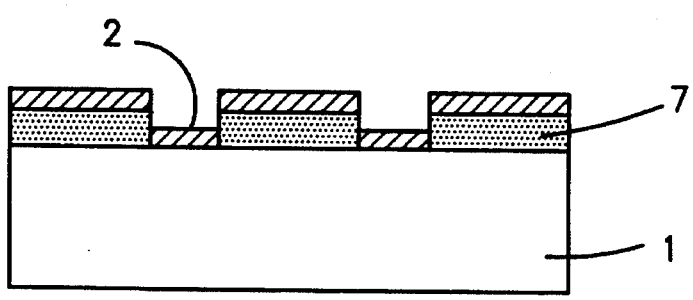

In this step, the support may be subjected to pretreatment with a reagent for enhancing adhesion of the photoresist, such as hexamethyl disilazane. Next, the thus treated support is subjected to irradiation with a mercury lamp through a photomask and then to development to effect patterning of the photoresist as shown in FIG. 6(b). Subsequently, the support is immersed in an aqueous acidic collagen solution (0.3 mg/ml) for 10 minutes and then washed with water to adsorb the collagen thereon, as shown in FIG. 6(c).

Figure 6D:
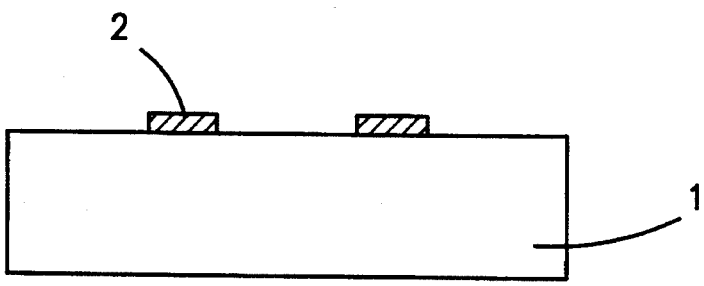

In the above process, the support may be subjected to a pretreatment with a reagent which imparts hydrophobicity to the surface of the support so as to enhance secure fixation of the collagen 2 to be adsorbed onto the quartz plate 1. The reagent to be used for such purpose includes, for example, polymeric compounds such as dimethyl polysiloxane and silane coupling agents such as octadecyl triethoxysilane. The photoresist is finally dissolved with an organic solvent, and the resulting support is washed with water to provide a cell culturing support as shown in FIG. 6(d).

In the above embodiment, the substance to be adsorbed onto the cell culturing support may not be limited to collagen, and any other substances which can specifically influence the culturing cells adhered onto the support and which has a property of being adsorbed onto the support can be used. According to the above embodiment, the substance which specifically influences the culturing cells can be introduced to the support at a high density.

FIGS. 7 (a) to (d) are a flow diagram illustrating a process for fabricating the cell culturing support according to another embodiment of the invention. The process will be described below step by step. A clarified quartz plate 1 is used as a support, and a photoresist 7 is first applied by spin coating and dried, as shown in FIG. 7(a).

Figure 7A:
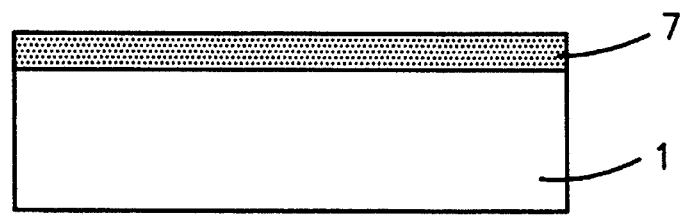
FIGS. 7(a) to (d) show a process for fabricating the cell culturing support according to another embodiment of the invention.
Figure 7B:
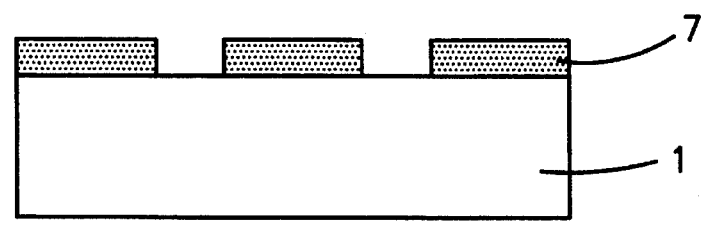

In this step, the support may be subjected to pretreatment with a reagent for enhancing adhesion of the photoresist, such as hexamethyl disilazane. Next, the thus treated support is subjected to irradiation with a mercury lamp through a photomask and then to development to effect patterning of the photoresist as shown in FIG. 7(b).

Figure 7C:
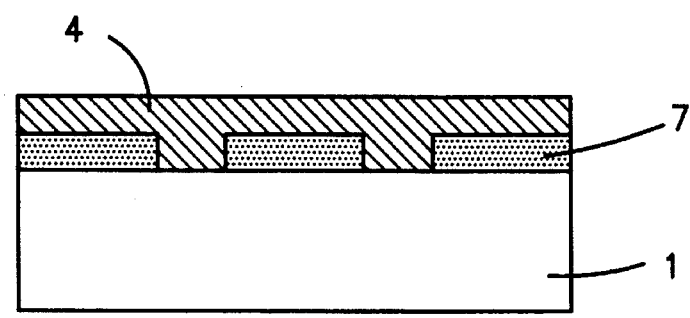
Figure 7D:
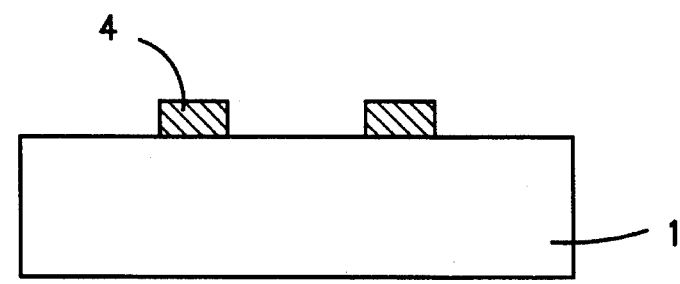

Subsequently, the support is coated by spin coating with an aqueous collagen solution (1.5 mg/ml) containing 1% of glutaraldehyde and then left to stand at room temperature for one hour to proceed a crosslinking reaction, followed by washing with water to form a crosslinked collagen film 4, as shown in FIG. 7(c). In this step, the support may be subjected to pretreatment with 3-aminopropyl triethoxysilane for enhancing adhesion of the crosslinked collagen film 4 to the quartz plate 1. The photoresist is finally dissolved with an organic solvent, and the resulting support is washed with water to provide a cell culturing support as shown in FIG. 7(d).

In the above embodiment, the film to be formed onto the cell culturing support may not be limited to collagen, and a film formed by crosslinking a cell-adhesive protein with a crosslinking agent can also be used.

Figure 8A:
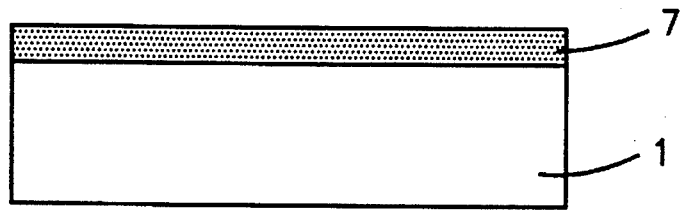
FIGS. 8 (a) to (d) show a process for fabricating the cell culturing support according to a further embodiment of the invention.
Figure 8B:
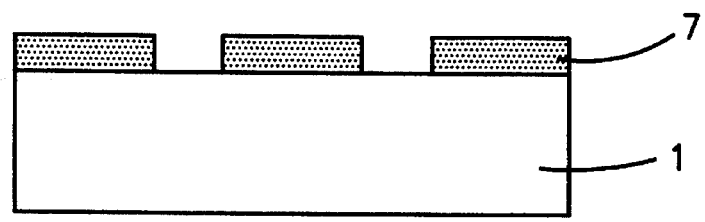

FIGS. 8(a) to (d) are a flow diagram illustrating a process for fabricating the cell culturing support according to a third embodiment of the invention. The process will be described below step by step. A clarified quartz plate 1 is first coated with a photoresist 7 by spin coating and dried, as shown in FIG. 8(a). In this step, the support may be subjected to pretreatment with a reagent for enhancing adhesion of the photoresist to the quartz plate 1, such as hexamethyl disilazane. Next, the thus treated support is subjected to irradiation with a mercury lamp through a photomask and then to development to effect patterning of the photoresist as shown in FIG. 8(b).

Figure 8C:
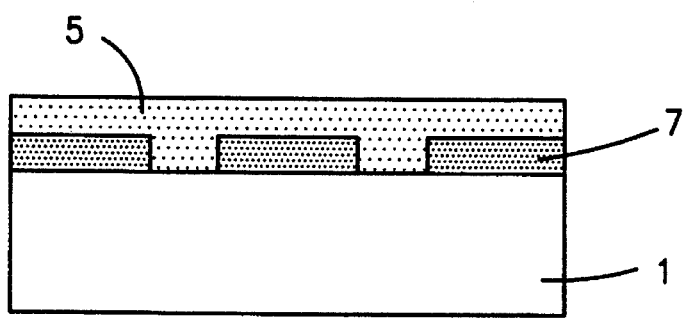

Subsequently, the support is coated by spin coating with a 15% aqueous bovine serum albumin solution containing 0.14% of collagen and 1% of glutaraldehyde and then left to stand at room temperature for one hour to proceed a crosslinking reaction, followed by washing with water to form a crosslinked albumin film 5 containing collagen, as shown in FIG. 8(c). In this step, the support may be subjected to pretreatment with a reagent for enhancing adhesion of the crosslinked albumin film 5 to the quartz plate 1, such as 3-aminopropyl triethoxysilane.

Figure 8D:
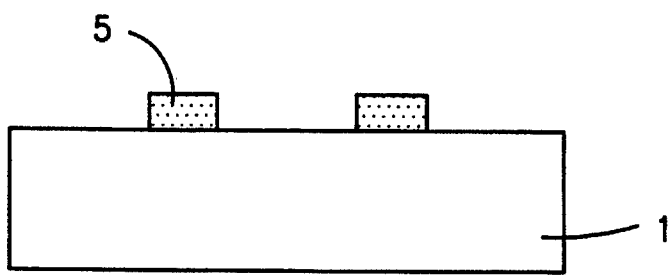

The photoresist is finally dissolved with an organic solvent, and the resulting support is washed with water to provide a cell culturing support as shown in FIG. 8(d). In the above embodiment, the substance to be contained in the crosslinked albumin film to be formed on the cell culturing support may not be limited to collagen, and any other substances which specifically influences the culturing cells adhered onto the support can also be used. The process according to the above embodiment of the invention enjoys an advantage in that a substance having a rather poor property of being adsorbed onto the support can readily be incorporated to the cell culturing support, since such substance is included in the crosslinked albumin film and fixed therein.

In each process for forming the cell culturing support according to the invention, the entire steps can be repeated or recombined to form a cell culturing support having a plurality of surfaces with different functions. For example, a cell culturing support having on the surface thereof a portion on which collagen is adsorbed and a portion on which an albumin film containing PVLA is formed can be fabricated.

As described heretofore, since the cell culturing support according to the present invention has a pattern formed by a substance or film which influences the cell adhesion rate or cell adhesion form, or crosslinked albumin films, cells can be adhered onto the desired positions of the support at a desired cell adhesion rate or in a desired cell adhesion form and cultured, and besides different kinds of cells can be adhered to different positions on the surface of the support.

On the other hand, according the process for fabricating the cell culturing support of the present invention, a substance or film which influences the cell adhesion rate or cell adhesion form, or crosslinked albumin films can be patterned at desired positions by means of photolithography.

Moreover, the present invention resorting to the lift-off method using a photoresist can also be applied to patterning of various kinds of other substances. In other words, the present invention enables control of not only the cell binding site but also activities or functions of the cells, facilitating application of the cultured cells to artificial internal organs and biosensors.

Although some of the embodiments of the present invention have been described herein, it should be apparent to those skilled in the art that the present invention may be embodied in many other specific forms without departing from the spirit or scope of the invention.

What is claimed is:

1. A cell culture support which provides for the adhesion and culturing of one or more types of adhesive cells which is produced by a process comprising:

(i) applying a photoresist onto a cell culture support surface and then partially removing the photoresist by photolithography;

(ii) pretreating the support surface from (i) with a reagent that imparts hydrophobicity to the support surface;

(iii) forming a crosslinked collagen film on the support surface from (ii); and (iv) dissolving the photoresist remaining on the support surface from (iii) to produce said cell culture support.

2. The cell culture support of claim 1 wherein the partial removal of the photoresist by photolithography is effected by treatment of the photoresist on the cell culture support surface by irradiation through a photomask and developing a irradiated photoresist under conditions which result in a predetermined patterning of the photoresist on the cell culture support surface.

3. The cell culture support of claim 1 wherein the cell culture support surface is pretreated with a reagent which facilitates adhesion at the photoresist prior to applying the photoresist into the cell culture support surface.

4. The cell culture support of claim 1 wherein the photoresist is removed by photolithography to provide for a striped, checkerboard or dotted pattern on the cell culture support surface.

5. The cell culture support of claim 1 wherein the photoresist layer is dissolved by treatment with an organic solvent and the cell culture support surface is then washed with water.

6. The cell culture support of claim 1 wherein the support contains cells adhered thereto.

7. A cell culture support which provides for the adhesion and culturing of one or more types of adhesive cells which is produced by a process comprising:

(i) applying a photoresist onto a cell culture support surface and then partially removing the photoresist by photolithography;

(ii) pretreating the support surface from (i) with a reagent that imparts hydrophobicity to the support surface;

(iii) forming a crosslinked collagen film on the support surface from (iii);

(iv) dissolving the photoresist remaining on the support surface from (iii); and (v) repeating the foregoing sequence of steps and in repeated step (iii) forming a film different in composition or thickness from the collagent film to produce said cell culture support.

8. The cell culture support of claim 7 wherein the partial removal of the photoresist by photolithography is effected by treatment of the photoresist on the cell culture support surface by irradiation through a photomask and developing the irradiated photoresist under conditions which result in a predetermined patterning of the photoresist on the cell culture support surface.

9. The cell culture support of claim 7 wherein the cell culture support surface is pretreated with a reagent which facilitates adhesion at the photoresist prior to applying the photoresist into the cell culture support surface.

10. The cell culture support of claim 7 wherein the photoresist is removed by photolithography to provide for a striped, checkerboard or dotted pattern on the cell culture support surface.

11. The cell culture support of claim 7 wherein the photoresist layer is dissolved by treatment with an organic solvent and the cell culture support surface is then washed with water.

12. A cell culture support which provides for the adhesion and culturing of one or more types of adhesive cells thereto which is produced by a process comprising:

(i) applying a photoresist onto a cell culture support surface and then partially removing the photoresist by photolithography;

(ii) pretreating the support surface from (i) with a reagent that imparts hydrophobicity to the support surface;

(iii) applying a solution comprising (a) collagen, (b) albumin, and (c) a crosslinking agent to the cell culture support surface under conditions providing for film formation; and (iv) dissolving the photoresist remaining on the cell culture support surface to produce said cell culture support.

13. The cell culture support of claim 12 wherein the partial removal of the photoresist layer by photolithography is effected by treatment of the photoresist on the cell culture support surface by irradiation through a photomask and developing the irradiated photoresist under conditions which result in a predetermined patterning of the photoresist on the cell culture support surface.

14. The cell culture support of claim 12 wherein the cell culture support surface is pretreated with a reagent which facilitates adhesion at the photoresist prior to applying the photoresist into the cell culture support surface.

15. The cell culture support of claim 12 wherein the photoresist is removed by photolithography to provide for a striped, checkerboard or dotted pattern on the cell culture support surface.

16. The cell culture support of claim 12 wherein the photoresist is dissolved by treatment with an organic solvent and the cell culture support surface is then washed with water.

17. A cell culture support which provides for the adhesion and culturing of one or more types of adhesive cells thereon which support is produced by a method comprising:

(i) applying a photoresist onto a cell culture support surface and then partially removing the photoresist by photolithography;

(ii) pretreating the support surface from (i) with a reagent which imparts hydrophobicity to the support surface;

(iii) applying a solution comprising (a) collagen, (b) albumin, and (c) a crosslinking agent to the cell culture support surface under conditions which provide for film formation;

(iv) dissolving the photoresist remaining on the cell culture support surface; and (v) repeating the foregoing sequence of steps and in repeated step (iii) using a solution which forms a film of a different composition or thickness from the film in step (iii) to produce said cell culture support.

18. The cell culture support of claim 17 wherein the partial removal of the photoresist by photolithography is effected by treatment of the photoresist on the cell culture support surface by irradiation through a photomask and developing the irradiated photoresist under conditions which result in a predetermined patterning of the photoresist on the cell culture support surface.

19. The cell culture support of claim 17 wherein the cell culture support surface is pretreated with a reagent which facilitates adhesion at the photoresist prior to applying the photoresist into the cell culture support surface.

20. The cell culture support of claim 17 wherein the photoresist is removed by photolithography to provide for a striped, checkerboard or dotted pattern on the cell culture support surface.

21. The cell culture support of claim 17 wherein the photoresist is dissolved by treatment with an organic solvent and the cell culture support surface is then washed with water.

* * * * *